United States Patent [19]

Knifton et al.

[11] Patent Number: 4,609,768

[45] Date of Patent: Sep. 2, 1986

[54] PROCESS FOR SYNTHESIS OF ETHYLENE GLYCOL FROM SYNTHESIS GAS PLUS 1,3-DIOXOLANE USING 1,3-DIOXOLANE AS A SOLVENT

[75] Inventors: John F. Knifton, Austin; Jiang-Jen Lin, Round Rock; Neal J. Grice, Austin, all of Tex.

[73] Assignee: Texaco Inc., White Plains, N.Y.

[21] Appl. No.: 663,602

[22] Filed: Oct. 22, 1984

[51] Int. Cl.$^4$ .................... C07C 29/00; C07C 31/20
[52] U.S. Cl. .................... 568/866; 568/678; 568/680
[58] Field of Search .................... 568/866

[56] References Cited

U.S. PATENT DOCUMENTS 2,421,862  6/1947  Arundale et al. .................... 568/831
4,356,332  10/1982  Knifton .................... 568/852

*Primary Examiner*—J. E. Evans
*Attorney, Agent, or Firm*—Jack H. Park; Kenneth R. Priem; Cynthia L. Kendrick

[57] ABSTRACT

This invention relates to the manufacture of ethylene glycol and more particularly to a low pressure process for making ethylene glycol comprising reacting synthesis gas, i.e. a mixture of carbon monoxide and hydrogen, plus 1,3-dioxolane in the presence of a homogenous liquid catalyst containing an effective amount of cobalt-containing compound, a silane or germane-containing promoter dispersed in a dioxolane solvent at a temperature of at least 50° C. and a pressure of at least 500 psi.

10 Claims, No Drawings

PROCESS FOR SYNTHESIS OF ETHYLENE GLYCOL FROM SYNTHESIS GAS PLUS 1,3-DIOXOLANE USING 1,3-DIOXOLANE AS A SOLVENT

This application is related to copending U.S. patent application Ser. Nos. 663,281, 663,284, and 663,280, filed of even date, the latter two now U.S. Pat. No. 4,565,896 and 4,568,780, respectively.

FIELD OF THE INVENTION

This invention relates to a new process for preparing ethylene glycol. More particularly, this invention relates to a novel process for preparing ethylene glycol in high yields from syngas which comprises contacting syngas, (a mixture of carbon monoxide and hydrogen), plus 1,3-dioxolane with a catalyst comprising a cobalt-containing compound and optionally a silane or germane promoter dispersed in 1,3-dioxolane as a solvent at a temperature of at least 50° C. and using moderate pressures of at least about 500 psig.

BACKGROUND OF THE INVENTION

Ethylene glycol is a chemical which has found wide use in industry. It is used, for example in the preparation of plasticizers for vinyl polymers and as a component in polyester fibers and antifreeze formulations. In view of its many uses, there is a need to find new and more economical methods for preparing ethylene glycol.

Proposed methods for making ethylene glycol involve the reaction of carbon monoxide with hydrogen in the presence of various proposed catalyst systems at elevated temperatures and pressures. For example, one of the earliest disclosed processes for making polyhydroxy compounds from readily available and inexpensive starting materials such as formaldehyde, carbon monoxide and hydrogen was disclosed in U.S. Pat. No. 2,451,333. The process comprised heating the starting materials with a reduced cobalt oxide hydrogenation catalyst under a high pressure, in excess of 100 atm. and at a temperature from about 80° C. to 300° C. Actually the examples in this patent used high pressures in the range of 500-800 atmospheres.

In Japan Kokai 76,128,903 (1976) to Mitsubishi a procedure is disclosed for preparing ethylene glycol by the reaction of CO, $H_2$ and HCHO with a cobalt catalyst containing a trivalent P, As or Sb compound at a temperature of about 160° C. and a pressure of about 180 $Kg/cm^2$, or approximately 2700 psi.

Similarly U.S. Pat. No. 4,144,401 uses CO, $H_2$ and formaldehyde as starting materials, but they are reacted in the presence of an alcohol solvent and a catalytic amount of rhodium or a rhodium-containing compound at a moderate temperature and pressure. Of course use of rhodium in a catalyst makes it expensive for commercial purposes. Methanol is also produced in substantial amounts in this process.

U.S. Pat. No. 4,356,332 pertains to the production of ethylene glycol by reaction of formaldehyde with carbon monoxide and hydrogen in the presence of a catalyst comprising a cobalt-containing compound and a tin-or germanium-containing promoter and in the presence of a substantially inert, oxygenated hydrocarbon solvent.

In U.S. Pat. No. 4,200,765 there is disclosed a process for preparing glycol aldehyde by reacting formaldehyde, hydrogen and carbon monoxide in an aprotic solvent at elevated temperatures and superatmospheric pressures in the presence of a rhodium catalyst with subsequent conversion of the glycol aldehyde to ethylene glycol by hydrogenation.

Japan Kokai 82,118,527 (1981) to Mitsubishi discloses the use of a ruthenium-based catalyst with a trivalent phosphorous compound to convert formaldehyde, CO and $H_2$ into ethylene glycol. The selectivity to ethylene glycol is not specified.

Japan Kokai 82,130,940 (1981) to Mitsui Petrochemicals employs a rhodium compound and an alkali metal compound. Again selectivity to ethylene glycol is not specified.

In U.S. Pat. No. 4,367,820 only carbon monoxide and hydrogen, without formaldehyde are used as starting materials for conversion to ethylene glycol via a catalyst comprising a cobalt-containing compound and a large excess of organosilicon compound. In most of the examples an operating temperature range of 250°–270° C. is employed, coupled with pressures of about 4000–8000 psi. Weight ratios of ethylene glycol to methanol were typically Ca. 2:1.

Additional Japanese applications disclose the use of a solution of formalin, carbon monoxide and hydrogen to produce ethylene glycol in the presence of a cobalt catalyst. See Japanese Application 197909 to Agency of Ind. Sci. Tech. In Jap. Application 188137 to the same agency, ethylene glycol is produced by reacting CO and hydrogen optionally with formaldehyde in the presence of a cobalt carbonyl and a phenol and/or alkylphenol.

Japanese Application 004782 (1981) to Mitsubishi discloses a process for producing ethylene glycol from formaldehyde, CO and $H_2$ in the presence of a catalyst containing ruthenium and a trivalent organo-phosphorous compound.

Finally in Japan Kokai Tokyo Koho JP 57,130,933 to Mitsubishi, acetals are reacted with CO and $H_2$ in the presence of a cobalt-iodine catalyst system to produce ethylene glycol.

Many of these processes require the use of high pressures (particularly in the absence of an added formaldehyde source), some use expensive rhodium-containing compounds and in most the selectivities for ethylene glycol are not very substantial and separation of the desired product is difficult.

The disclosure of a process for producing ethylene glycol from simple starting materials such as syngas (i.e. carbon monoxide and hydrogen) and 1,3-dioxolane by reacting the starting materials in the presence of a catalyst compound which would be relatively inexpensive, even on a commercial sale, and which could be reacted at low temperatures and pressures therefore allowing for less expense in construction of reactors, etc. would be an advance in the art, especially if the selectivity for ethylene glycol were better than found in previous work.

SUMMARY OF THE INVENTION

This invention concerns a process for making ethylene glycol comprising contacting a mixture of synthesis gas, i.e., carbon monoxide and hydrogen, plus 1,3-dioxolane with a catalyst comprising a cobalt-containing compound and optionally a silane or germane-containing compound dispersed in 1,3-dioxolane as a catalyst solvent and heating the resultant mixture at a temperature of at least 50° C. and a pressure of at least 500 psi for sufficient time to produce the desired ethylene glycol. By using this catalyst system one can obtain a high concentration of ethylene glycol in the crude product liquids, the process can be operated at moderate temperatures and pressures and the use of extreme conditions and expensive catalyst compounds required in many of the prior known processes can be avoided. Further, the process provides for ease of separation of the glycol products.

The process of the invention, as far as the formation of the desired ethylene glycol is concerned, may be represented by the following equation:

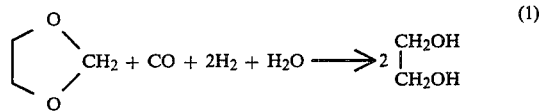

(1)

Typical concentrations of ethylene glycol in the crude liquid product range up to 69.1 wt %, typical yields of ethylene glycol (basis 1,3-dioxolane charged) range up to 70 mole %. Total glycol products may comprise up to 77.1 wt % of the crude liquid. Another surprising result of the process is that there is essentially no competing water gas shift or methanation activity.

DETAILED DESCRIPTION OF THE INVENTION

In the operation of the process of the invention, ethylene glycol is prepared from a synthesis gas mixture of carbon monoxide and hydrogen plus 1,3-dioxolane by a process comprising the following steps:

(a) contacting said mixture of carbon monoxide, hydrogen and 1,3-dioxolane with a catalyst comprising a cobalt-containing compound and optionally a silane or germane-containing compound dispersed in 1,3-dioxolane as the catalyst solvent;

(b) heating said mixture to a temperature of at least 50° C. under a pressure greater than 500 psi and with sufficient carbon monoxide and hydrogen to satisfy the above-noted stoichiometry of the desired ethylene glycol synthesis until substantial formation of the desired ethylene glycol has been achieved; and (c) preferably isolating said ethylene glycol by fractional distillation from the crude liquid and recycling the bottom liquid containing the cobalt catalyst.

In order to present the inventive concept of the present invention in the greatest possible detail, the following supplementary disclosure is submitted. The process of the invention is practiced as follows:

As noted, the new catalyst system used in the process of the invention contains a cobalt-containing compound and a silane or germane-containing promoter. The cobalt compound to be used may be chosen from a wide variety of organic and inorganic compounds, complexes, etc. It is only necessary that the catalyst employed contain the cobalt in any of its ionic states.

The cobalt-containing compound employed may take many different forms. For instance the cobalt may be added to the reaction mixture in an oxide form as in the case of, for example, cobalt(II) oxide, (CoO) or cobalt-(II,III) oxide ($Co_3O_4$) Alternatively, it may be added as the salt of a mineral acid, as in the case of cobalt(II) nitrate hydrate ($Co(NO_3)_2.6H_2O$), cobalt(II) phosphate, cobalt(II) sulfate, etc. or as the salt of a suitable organic carboxylic acid, for example, cobalt(II) formate, cobalt-(II) acetate, cobalt(II) propionate, cobalt naphthenate, or bonded to a carbonyl-containing ligand as in the case of cobalt acetylacetonate, etc. The cobalt may also be added to the reaction zone as a carbonyl or hydridocarbonyl derivative. Here, suitable examples include dicobalt octacarbonyl, ($Co_2(CO)_8$), cobalt hydridocarbonyl, ($HCo(CO)_4$) and substituted carbonyl species such as the organophosphorus cobalt carbonyls like $HCo(CO)_3$-($Bu_3P$).

Preferred cobalt-containing compounds include oxides of cobalt, cobalt salts of mineral acids, cobalt salts of organic carboxylic acids and cobalt carbonyl or hydridocarbonyl derivatives. Among these, particularly preferred are dicobalt octacarbonyl, cobalt(II) oxide, cobalt(II) nitrate, cobalt acetylacetonate and cobalt(II) acetate.

The optional silane or germane-containing promoter employed in the practice of this invention may also take many different forms. Generally, the silicon-containing promoter should contain at least one bond between a silicon atom and a carbon atom, but suitable organosilicon compounds may comprise mono-, di-, tri- and tetraorgano groups bonded to silicon. Each organo group may be an alkyl, aryl or aryalkyl moiety, having one to 20 carbon atoms. The silicon-containing promoter may also contain silicon-oxygen bonds, and preferred promoters are halogen-free silanes containing at least one silicon-hydrogen bond per molecule.

Typical examples of organosilicon compounds that are suitable for use in the process of equation (1) include trialkylsilanes, such as triethylsilane ($Et_3SiH$), tricyclohexylsilane [($C_6H_{11})_3SiH$], trimethylsilane, tri-n-hexylsilane and methyldiethylsilane ($MeEt_2SiH$), as well as dimethylethylsilane and the tripropylsilanes, the dialkylsilanes such as diethylsilane ($Et_2SiH_2$) and dimethylsilane, the tetraalkylsilanes such as tetramethylsilane and tetraethylsilane, the arylsilanes such as triphenylsilane ($Ph_3SiH$), diphenylsilane and hydroxytriphenylsilane, as well as the alkoxysilanes such as triethoxysilane [($EtO)_3SiH$], phenyltriethoxysilane, tetraethoxysilane and tetramethoxysilane. Less satisfactory are the halogenated organosilanes such as chlorotrimethylsilane, dimethylsilane chloride ($Me_2SiHCl$), chlorotriphenylsilane, dichlorodimethylsilane ($Me_2SiCl_2$), chlorotriethylsilane, and iodotrimethylsilane. Other suitable organosilicon promoters containing at least one silicon-hydride bond, and more than one silicon atom per molecule, include:

H₃SiCH₂SiH₃
H₃SiCH₂CH₂SiH₃
CH₃SiH₂CH₂SiH₃

CH₃SiH₂CH₂SiH₂
|
CH₃SiH₂CH₂

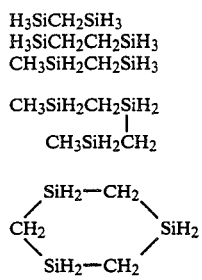

Suitable silanes containing more than one silicon-hydride bond per molecule are exemplied by:

C₆H₁₃SiH₃
CH₃CH=CHCH₂SiH₃

CH₂=CHCHSiH₃
|
CH₃

CH₂=CHCH₂SiH₃
C₆H₅CH₂CH₂SiH₃
C₆H₅CH(CH₃)SiH₃
(C₃H₇)₂SiH₂
(CH₃)(isoC₄H₉)SiH₂
(C₂H₅)(isoC₄H₉)SiH₂
(CH₂=CH)(C₂H₅)SiH₂
(CH₂=CH)(C₄H₉)SiH₂

Also effective as silicon-containing promoters in the practice of this process are siloxanes and polyalkylsiloxanes. These may include hexaethyldisiloxane, hexamethylcyclotrisiloxane, octamethylcyclotetrasiloxane, hexamethyldisiloxane, tetramethyldisiloxane (Me₂HSiOSiHMe₂), methylhydrocyclosiloxane, as well as alkylsiloxane polymers of the type:

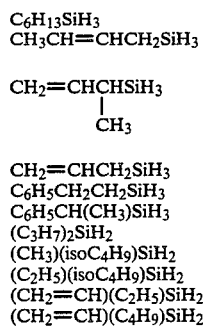

wherein R is one or different alkyl groups containing 1 to 6 carbon atoms.

Equally useful are the higher M.W. tetraalkylsilanes and tetraalkoxysilanes wherein each alkyl or alkoxy group contains 1 to 20 carbon atoms, and each alkyl group may have the same or different carbon number.

Preferred organosilane compounds include triethylsilane, triphenylsilane, trimethylsilane, diphenylsilane, tricyclohexylsilane, tetramethylsilane, tetraethylsilane, hydroxytriphenylsilane, diethylsilane and tripropylsilane.

The germanium-containing compound which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbylgermanium compound such as tetra-n-butylgermane, tetraethylgermane, tetraphenylgermane and tetramethylgermane, or an organohalide germanium compound such as diphenylgermanium chloride, methylgermanium trichloride, phenylgermanium trichloride, tri-n-butylgermanium iodide, triethylgermanium chloride, triethylgermanium iodide, trimethylgermanium chloride, triphenylgermanium bromide and triphenylgermanium chloride, or as an organogermanium hydride, such as triphenylgermanium hydride, or as an organogermanium oxide or carboxylate such as triphenylgermanium acetate, or as a germanium alkoxide such as germanium butoxide, germanium ethoxide and germanium methoxide.

The preferred germanium-containing promoter compounds are the organo-halide germanium compounds, the hydrocarbyl germanium compounds, and the organogermanium hydrides. Among these, particularly preferred are triphenylgermanium bromide, trimethylgermanium bromide, triphenylgermanium hydride, tetraphenylgermane, tetraethylgermane and triethylgermanium chloride.

As characterized above, this process is operated as a homogeneous liquid phase mixture. For excellent results in the process of this invention, the cobalt-based homogeneous catalyst combinations involving the use of organosilane and organogermane promoters, can be solubilized in the 1,3-dioxolane coreactant (eq. 1) for an improvement in production of ethylene glycol. Percentages of ethylene glycol are as much as 10 wt % higher than found in, for example, copending application Ser. No. 663,280.

The quantity of cobalt-containing compound and the optional silane or germane-containing compound to be used in the process of the invention may vary. The process is conducted in the presence of a catalytically effective quantity of the active cobalt-containing compound and the active silane or germane-containing compound which gives the desired product in a reasonable yield. The reaction proceeds when employing as little as about $10^{-2}$ weight percent, and even lesser amounts of the cobalt-containing compound, together with as little as about 30 weight percent of dioxolane solvent, based on the total weight of the reaction mixture. The upper concentration is dictated by a variety of factors including catalyst cost, partial pressures of carbon monoxide and hydrogen, operating temperature, etc. A cobalt-containing compound concentration of from about $10^{-2}$ to about 30 weight percent in conjunction with a silane or germane-containing compound concentration of from zero to about 50 percent and a dioxolane solvent concentration of from about 10 to about >95 weight percent, based on the total weight of the reaction mixture is generally desirable in the practice of this invention.

Particularly superior results are obtained when the above-noted components of the catalyst system are combined as follows on a molar basis: cobalt-containing compounds to silane or germane-containing compound of 1:0.1 to 1:100.

The temperature range which can be employed in the process of the invention may vary over a considerable range depending upon experimental factors, including the choice of catalyst, pressure and other variables. A preferred range of operability is from about 50° C. to about 350° C. when superatmospheric pressures of syngas are employed. A narrower range of about 100° C. to 220° C. represents a preferred temperature range. Best results are generally observed in the range of 160° C.–200° C.

The pressure employed may also vary over a considerable range, but in most cases is at least above 500 psig. A preferred operating range varies from about 1000 psig to about 6000 psig, although pressures above 6000 psig also provide useful yields of the desired product. The pressures referred to herein represent the total pressure generated by all the reactants, although they are substantially due to the carbon monoxide and hydrogen fractions. In the presence of 1,3-dioxolane, the total pressures required for glycol syntheses using cobalt silane or germane-promoted catalyst systems are normally lower than those pressures required for direct glycol production from CO/$H_2$ (See, for example, U.S. Pat. No. 4,367,820).

The relative amounts of carbon monoxide, hydrogen which can be initially present in the syngas mixture are variable, and these amounts may be varied over a wide range. In general, the mole ratio of CO:$H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide, hydrogen and 1,3-dioxolane present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The most desired product of this synthesis, ethylene glycol (EG) will be formed in significant quantities (up to Ca. 69.1 wt % concentration in the crude liquid product) and up to 70 mole % yield (basis total 1,3-dioxolane charged) using the cobalt-silicon or germane promoted catalyst system of this invention. Also formed are significant amounts of diethylene glycol (DEG), propylene glycol (PG), together with derivatives such as the ethylene glycol monoalkyl ethers (e.g. ethylene glycol monomethyl ether, EGMME). Selectivity to total glycol products (EG+DEG+PG+EGMME) may exceed 77 wt %. Lower monohydric alcohols-methanol and ethanol are also present in the crude liquid product mix. Each of these product oxygenates, including ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in pounds per square inch gauge (psig).

The yield of ethylene glycol in each synthesis (mole %) is estimated basis equation 1 using the formula:

$$\frac{\text{Total Ethylene Glycol Produced (mmole)}}{[\text{Total 1,3-dioxolane charged (mmole)}] \times 2} \times 100$$

Total liquid product increase (wt %) is estimated basis:

$$\frac{(\text{Total Liquid + Solid Product, g}) - (\text{Total Catalyst + 1,3-Dioxolane Charged, g})}{(\text{Total Catalyst + 1,3-Dioxolane Charged, g})} \times 100$$

To illustrate the process of the invention, the following examples are given. It is to be understood, however, that the examples are given in the way of illustration and are not to be regarded as limiting the invention in any way.

EXAMPLE I

A 450 ml capacity reactor with glass liner was charged with a mixture of dicobalt octacarbonyl (12.0 mmole Co, 2.052 g), triethylsilane (24.0 mmole, 2.790 g) in 1,3-dioxolane (400 mmole, 29.63 g) and water (200 mmole, 3.60 g). The mixture was flushed with nitrogen, the reactor sealed, flushed with synthesis gas (CO/$H_2$, 1:2), pressured to 2700 psi with CO/H2 (1:2), and heated to 160° C. with agitation. After four hours, the reactor was allowed to cool, the gas pressure (1775 psig) noted, and the excess gas sampled and vented.

43.2 g of a red liquid, two phase, product was recovered. There was no solid precipitate at this stage.

Analysis of the liquid product shows the lighter phase (3.5 ml) to be primarily silane. The heavier phase (37 ml) was found to comprise:
- 69.1 wt % ethylene glycol (EG)
- 4.4 wt % ethylene glycol monomethyl ether (EGMME)
- 0.9 wt % propylene glycol (PG)
- 2.7 wt % diethylene glycol (DEG)
- 11.5 wt % water
- 1.1 wt % methanol
- <0.1 wt % unreacted 1,3-dioxolane Estimated conversion of the 1,3-dioxolane charged was >98%.

Estimated amount of ethylene glycol produced was 449 mmole.

Estimated amount of glycol products (EG+EGMME+PG+DEG) was 476 mmole.

Typical gas samples comprise:
- 65% hydrogen
- 35% carbon monoxide

Cobalt recovery in solution was >98%

EXAMPLE II

In this Example, the dicobalt octacarbonyl-triethylsilane catalyst is used at an initial cobalt:silicon molar ratio of Ca. 1:11.

Following the procedure of Example I, a 450 ml capacity reactor with glass liner was charged with a mixture of dicobalt octacarbonyl (12.0 mmole Co, 2.052 g), triethylsilane (129 mmole, 15.0 g) in 1,3-dioxolane (400 mmole, 29.63 g) and water (200 mmole, 3.60 g). The mixture was flushed with nitrogen, the reactor sealed, flushed with synthesis gas (CO/$H_2$, 1:2), pressured to 2700 psi with CO/$H_2$ (1:2), and heated to 160° C. with agitation. After four hours, the reactor was allowed to cool, the gas pressure (1600 psig) noted, and the excess gas sampled and vented.

53.6 g of a two phase liquid product was recovered. There was no solid precipitate at this stage.

The lighter phase (19 ml, red liquid) was primarily silane. The heavier phase (34 ml) was found to comprise:
- 57.9 wt % ethylene glycol (EG)
- 8.8 wt % ethylene glycol monomethyl ether (EGMME)
- 0.7 wt % propylene glycol (PG)
- 5.3 wt % diethylene glycol (DEG)
- 10.2 wt % water
- 2.5 wt % methanol
- 0.3 wt % unreacted 1.3-dioxolane

EXAMPLE III

In this example the differences include the mmoles of water used, the operating pressure and the temperature. The pressure and temperature used constitute forcing conditions which allow for improved yields of glycol. It is noted that 1,3-dioxolane and water are used in a 1:1 molar mix.

A 450 ml capacity reactor with glass liner was charged with a mixture of dicobalt octacarbonyl (12.0 mmole Co, 2.052 g), triethylsilane (24.0 mmole, 2.790 g) in 1,3-dioxolane (400 mmole, 29.63 g) and water (400 mmole, 7.2 g). The mixture was flushed with synthesis gas (CO/$H_2$, 1:2), sealed and pressured to 2000 psi with CO/$H_2$ (1:2), heated to 180° C. with agitation and the pressure raised to 5000 psi. Pressure was maintained at 5000 psi by intermittent addition of syngas (1:2) from a large surge tank. After four hours, the reactor was allowed to cool, and the excess gas vented.

46.8 g of a two phase liquid product was recovered. There was no solid precipitate at this stage.

Analysis of the liquid product shows the lighter phase (2 ml red liquid) to be primarily silane, while the heavier phase (41 ml, red liquid) contains:
- 66.7 wt % ethylene glycol (EG)
- 2.9 wt % ethylene glycol monomethyl ether (EGMME)
- 0.9 wt % propylene glycol (PG)
- 2.6 wt % diethylene glycol (DEG)
- 19.9 wt % water
- 1.4 wt % methanol
- 0.2 wt % unreacted 1,3-dioxolane Estimated conversion of the 1,3-dioxolane charged was >98%.

Estimated amount of ethylene glycol produced is 481 mmole.

Estimated amount of glycol products (EG+EGMME+PG+DEG) was 514 mmole.

Cobalt recovery in solution was >98%.

COMPARATIVE EXAMPLE IV

In this example it will be noted that glycol can be generated in high concentrations from CO/$H_2$ plus 1,3-dioxolane in the presence of dicobalt octacarbonyl but without the use of the triethyl silane promoter.

Following the procedure of the previous examples, the reactor was charged with dicobalt octacarbonyl (12.0 mmole CO, 2.052 g), 1,3-dioxolane (400 mmole) and water (200 mmole). There was no silane fraction in this example. The mixture was pressured to 2700 psi with CO/$H_2$ (1:2), heated to 160° C. and held at temperature for 4 hours with agitation.

41.4 g of a red liquid product was recovered. Analysis of this liquid product showed it to contain:
- 64.3 wt % ethylene glycol (EG)
- 4.6 wt % ethylene glycol monomethyl ether (EGMME)
- 0.8 wt % propylene glycol (PG)
- 3.1 wt % diethylene glycol (DEG)
- 11.5 wt % water
- 1.3 wt % methanol
- 0.1 wt % unreacted 1,3-dioxolane

EXAMPLE V

A typical cobalt-silane catalyst solution was prepared as follows:

1,3-dioxolane (1151.4 g, 15.5 mole) was stirred under carbon monoxide purge for 30 minutes, dicobalt octacarbonyl (80.0 g, 0.234 mole) was added followed by triethylsilane (108.9 g, 0.936 mole) addition from a dropping funnel. With a minimum of delay, deionized water (280.4 g, 15.5 mole) was added from a dropping funnel, with vigorous gas evolution being carefully controlled during the initial addition. After all the water had been added, the mixture was stirred under CO atmosphere for about one hour until gas evolution ceased, and filtered through celite under a CO blanket.

Cobalt concentration in the resulting clear red solution=2.96%.

EXAMPLE VI

In this Example, ethylene glycol was prepared from 1,3-dioxolane and syngas in continuous unit equipment using the cobalt-silane catalyst solution of Example V.

A 300 ml stirred-tank reactor, fitted with continuous gas and liquid feed pumps and the necessary temperature and pressure controls, was fed the liquid cobalt octacarbonyl-triethylsilane/aqueous 1,3-dioxolane solution prepared as above, at a rate of 16 ml/hr, from a ruska pump. Synthesis gas (2:1, $H_2$/CO) was also fed to the reactor at a rate of 42 stpl/hr. Reactor temperature was held at 180° C., and the total pressure was maintained at 4000 psi. The liquid product was collected in an ice-cooled receiver followed by two dry ice/acetone traps. The ruska pump was refilled from a larger feed tank containing the cobalt-silane-1,3-dioxolane solution of Example V under a CO atmosphere, as necessary.

Analysis of the liquid product effluent (22.7 g/hr) by glc showed it to comprise:

- 67.8 wt % ethylene glycol (EG)
- 3.8 wt % ethylene glycol monomethyl ether (EGMME)
- 0.4 wt % propylene glycol (PG)
- 2.2 wt % diethylene glycol (DEG)
- 0.7 wt % methanol
- 13.8 wt % water
- 3.4 wt % unreacted 1,3-dioxolane

What is claimed is:

1. A process for making ethylene glycol comprising reacting synthesis gas, a mixture of carbon monoxide and hydrogen, plus 1,3-dioxolane in the presence of a liquid catalyst consisting essentially of an effective amount of cobalt-containing compound and a silane-containing promoter, dispersed in a dioxolane solvent at a temperature of at least 50° C. and a pressure of at least 500 psi.

2. The process of claim 1, wherein the cobalt-containing compound is selected from the group consisting of cobalt oxides, cobalt salts of a mineral acid, cobalt salts of a carboxylic acid and cobalt carbonyl or hydrocarbonyl derivatives.

3. The process of claim 2, wherein the cobalt-containing compound is from the group consisting of dicobalt octacarbonyl, cobalt(II) oxide, cobalt(II) nitrate, cobalt(II) acetate or cobalt acetylacetonate.

4. The process of claim 3, wherein the cobalt-containing compound is dicobalt octacarbonyl.

5. The process of claim 1, wherein the silane-containing promoter is selected from the group consisting of triethylsilane, triphenylsilane, hydroxytriphenylsilane, diphenylsilane, tricyclohexylsilane and tetramethylsilane.

6. The process of claim 5, wherein the silane-containing promoter is selected from the group consisting of triethylsilane and triphenylsilane.

7. The process of claim 1, wherein the temperature is between 50° C. and 350° C.

8. The process of claim 1, wherein the temperature is between about 100° C. and 220° C.

9. The process of claim 1, wherein the pressure is between 1000 psi and 6000 psi.

10. A process for making ethylene glycol which comprises reacting synthesis gas, a mixture of carbon monoxide and hydrogen, plus 1,3-dioxolane in the presence of a homogenous liquid catalyst consisting essentially of an effective amount of cobalt-containing compound selected from the group consisting of cobalt oxides, cobalt salts of a mineral acid, cobalt salts of a carboxylic acid and cobalt carbonyl or hydrocarbonyl derivatives, and a promoter from the group consisting of triethylsilane, triphenylsilane, hydroxytriphenylsilane, diphenylsilane, tricyclohexylsilane and tetramethylsilane dispersed in 1,3-dioxolane solvent, at a temperature of 100° C. to 220° C. and a pressure of 1000 psi to 6000 psi wherein the molar ratio of cobalt to silane promoter is 1:0.1 to 1:100.

* * * * *